United States Patent
Raja et al.

(10) Patent No.: US 8,450,526 B2
(45) Date of Patent: May 28, 2013

(54) AMMOXIMATION PROCESS

(75) Inventors: Robert Raja, Eastleigh (GB); John Meurig Thomas, Cambridge (GB)

(73) Assignee: University of Southhampton, Southhampton (GB)

( * ) Notice: Subject to any disclaimer, the term of this patent is extended or adjusted under 35 U.S.C. 154(b) by 93 days.

(21) Appl. No.: 12/666,343

(22) PCT Filed: Jul. 2, 2008

(86) PCT No.: PCT/GB2008/002286
§ 371 (c)(1),
(2), (4) Date: Feb. 12, 2010

(87) PCT Pub. No.: WO2009/004342
PCT Pub. Date: Jan. 8, 2009

(65) Prior Publication Data
US 2010/0179317 A1    Jul. 15, 2010

(30) Foreign Application Priority Data
Jul. 3, 2007 (GB) .................................. 0712903.4

(51) Int. Cl.
*C07C 249/04* (2006.01)
(52) U.S. Cl.
USPC ......................................................... 564/267
(58) Field of Classification Search
USPC .................................. 540/535, 536; 564/267
See application file for complete search history.

(56) References Cited

U.S. PATENT DOCUMENTS

| | | |
|---|---|---|
| 4,567,029 A | 1/1986 | Wilson et al. |
| 4,801,364 A | 1/1989 | Wilson et al. |
| 4,894,478 A | 1/1990 | Roffia et al. |
| 4,917,876 A | 4/1990 | Lok et al. |
| 4,956,165 A | 9/1990 | Lok et al. |

OTHER PUBLICATIONS

Raja R et al: "Bifunctional Molecular Sieve Catalysts for the benign ammoximation of cyclohexanone: one-step solvent-free production of oxime and caprolactam with a mixture of air and ammonia" Journal of the American Chemical Society, American Chemical Society, Washington, DC.; US, US, vol. 123, Jan. 1, 2001 schemes 1 and 2 first paragraph, pp. 8153-8154.
Robert Mokaya et al.: A cleaner way to nylon? Nature, vol. 437, No. 27; 2005, pp. 1243-1244, XP002504232 p. 1243, left column, last paragraph, middle column second paragraph.
Jihong Yu et al.: "Rich structure chemistry in the aluminophosphate family" Acc. Chem. Res., vol. 36, 2003, pp. 481-490, XP002504233, the whole document.
Lipeng Zhou et al.: Synthesis of FeCoMnAPO-5 molecule sieve and catalytic activity in cyclohexane oxidation by oxygen, Catalysis Letters vol. 99, Nos. 3-4, Feb. 2005, pp. 231-234.
International Search Report dated Nov. 28, 2008.
GB Search Report dated Nov. 2, 2007.

*Primary Examiner* — Bruck Kifle
(74) *Attorney, Agent, or Firm* — Banner & Witcoff, Ltd.

(57) ABSTRACT

A redox ammoximation process in which a ketone or aldehyde is reacted with ammonia and oxygen in the presence of a catalyst; wherein the catalyst is an aluminophosphate based redox catalyst having at least two different redox catalytic sites comprising different transition metal atoms.

5 Claims, No Drawings

AMMOXIMATION PROCESS

The present invention relates to an ammoximation process using a redox catalyst comprising an aluminophosphate, commonly referred to as an "AlPO" system.

AlPO compounds are well known and are known for use as molecular sieves and as catalysts for various processes, for example as described in U.S. Pat. No. 4,567,029, EP0132708, U.S. Pat. Nos. 5,000,931, 4,801,364, 5,107,052, 4,853,197, EP0293920, U.S. Pat. Nos. 6,293,999, and 6,296,688. They are nanoporous solids with channels permeating the whole of the material, thus giving the material a very substantial surface area, which can be used for catalysis. The basic structure comprises aluminium and oxygen atoms, in which some of the aluminium atoms have been replaced by one or more other atoms, to provide the required catalytic activity.

J. M. Thomas & R. Raja, [*Design of a "green" one-step catalytic production of ε-caprolactam (precursor of nylon-6)*, Proceedings Natl. Acad. Sci. USA, 102, 13732-13736 (2005)]; R. Raja, G. Sankar & J. M. Thomas, [*Bifunctional molecular sieve catalysts for the benign ammoximation of cyclohexanone: One-step, solvent-free production of oxime and ε-caprolactam with a mixture of air and ammonia*, J. Am. Chem. Soc. 123, 8153-8154 (2001)]; and Nature (October 2005, Vol. 437; page 1243) describe a process for preparing certain precursors to nylon, especially ε-caprolactam, using such AlPO catalysts, specifically AlPO catalysts having at least two active sites, one being a redox site, generally based upon Co(III), Mn(III) or Fe(III) atoms, and the other being a Brønsted acid site, generally based on Zn(II), Mg(II) or Co(II) atoms. The two types of site are well separated in the three dimensional AlPO structure and operate separately on the feedstock. As a result, it is possible to convert the cyclohexanone feedstock into ε-caprolactam with an efficiency in excess of 70%, up to around 80%, in a single step, rather than use the multi-step procedure currently used—see Nature (op cit).

However, for commercial purposes, a 70% conversion is inadequate, and so, although the reaction proposed in the above literature is very elegant and of considerable scientific interest, it is presently of little commercial value.

Furthermore, there is a desire to produce compounds which can act as intermediates for other useful products. These intermediates include oximes, especially cyclohexanone-oximes.

We have now surprisingly found that a modification of the catalyst used in the reaction described above is capable of carrying out ammoximation with a better yield of up to 100% efficiency. The resulting oxime may then be converted efficiently, using well known reactions, to the desired ε-caprolactam. Surprisingly, the two-step reaction is substantially more efficient than the one-step reaction described in the above papers.

The present invention provides a redox ammoximation process in which a ketone or aldehyde is reacted with ammonia and oxygen in the presence of a catalyst; wherein the catalyst is an aluminophosphate based redox catalyst having at least two different redox catalytic sites comprising different transition metal atoms. The catalyst may, for example, be represented by the following qualitative general formula (I) or (II):

$$M^1M^2AlPO \quad (I)$$

or (II):

$$M^1M^2SAlPO \quad (II)$$

in which: $M^1$ and $M^2$ are different from each other and each represents a metal atom having redox catalytic capability, and some of the phosphorus [P(V)] atoms may be replaced by other equivalent atoms. It should be noted that these formulae are purely an indication of the nature of the atoms present and do not represent their relative proportions.

Examples of metals which may be represented by $M^1$ and $M^2$ include Co(III), Mn(III), Fe(III), Ti(IV), Cr(VI), Cu(III), V(V) and Ru(III).

Some preferred catalyst combinations include (but are not limited to):

(a) $M^1M^2$AlPO-5 where $M^1$≡Mn(III) and $M^2$≡Co(III) or Fe(III) or Ru(III);

(b) $M^1M^2$SAPO-5, where $M^1$≡Co(III), $M^2$≡Mn(III) and additionally $P^V$ can be replaced with Ti(IV), Cr(VI) or V(V);

(c) $M^1M^2$AlPO-36 where $M^1$≡Co(III) and $M^2$≡Mn(III) or Fe(III) or Ru(III);

(d) $M^1M^2$SAPO-36, where $M^1$≡Mn(III), $M^2$≡Fe(III) and additionally $P^V$ can be replaced with Ti(IV), Cr(VI) or V(V);

(e) $M^1M^2$AlPO-31 where $M^1$≡Fe(III) and $M^2$≡Co(III) or Mn(III) or Ru(III);

(f) $M^1$ $M^2$SAPO-31, where $M^1$≡Co(III), $M^2$≡Fe(III) and additionally $P^V$ can be replaced with Ti(IV), Cr(VI) or V(V);

(g) $M^1$ $M^2$SAPO-18, where $M^1$≡Co(III), $M^2$≡Mn(III) and additionally. $P^V$ can be replaced with Ti(IV), Cr(VI) or V(V);

(h) $M^1M^2$AlPO-18 where $M^1$≡Mn(III) and $M^2$≡Co(III) or Fe(III) or Ru(III);

(i) $M^1$ $M^2$SAPO-37, where $M^1$≡Mn(III), $M^2$≡Co(III) and additionally $P^V$ can be replaced with Ti(IV), Cr(VI) or V(V);

(j) $M^1M^2$AlPO-37 where $M^1$≡Fe(III) and $M^2$≡Co(III) or Fe(III) or Ru(III).

Catalysts of this type are known and processes for their preparation are equally known. Catalysts containing a single redox catalyst site are described, for example, in U.S. Pat. No. 4,567,029, "Catalytically active centres in porous oxides: design and performance of highly selective new catalysts", J. M. Thomas and R. Raja, Chem. Comm., 2001, 675-687 and "Design of a green one-step catalytic production of ε-caprolactam (precursor of nylon-6)", J. M Thomas and R. Raja, PNAS, Vol 102/39), 13732-13736. The catalysts with two redox sites can be prepared in a similar manner. Catalysts with two or more redox sites are described in U.S. Pat. Nos. 4,956,165, 4,917,876, 4,801,364 and 4,567,029.

In outline the procedure is as follows: the phosphorous source (typically 85% $H_3PO_4$) and the requisite amount of distilled deionised $H_2O$ are first mixed, for example gently stirred (400 rpm), for example using a mechanical stirrer in a Teflon-lined autoclave. To this the aluminium source (typically $Al(OH)_3$) is added, preferably slowly. The two redox metal sources ($M^1$ and $M^2$) are dissolved in water and then added, preferably slowly, to the previously prepared Al—$H_3PO_4$ mixture (preferably under stirring). An appropriate (depending on the desired structure-type) template (structure-directing agent) is then introduced, drop wise, under vigorous stirring (e.g. at 1700 rpm) and the gel is aged, for example, for about 1-2 hours at 298 K. The gel is then heated in order to synthesize a desired structure-type, for example it may be sealed in the Teflon-lined stainless steel autoclave and heated to the desired temperature, under autogenous pressure, for the required amount of time. The solid product is isolated, preferably by filtration or centrifugation (after crystallization), washed with copious amounts of distilled deionised water and dried under vacuum (90-120° C.). The as-prepared product is calcined for example at 550° C., first in nitrogen for 4 hours and then in dry oxygen for 16 hours, before its use as a catalyst.

Phase purity, structural integrity and crystallinity of the final catalyst may be confirmed by using a combination of powder x-ray diffractometry (XRD), X-ray absorption spectroscopy (XAS) and high resolution electron tomography. The precise stoichiometry (with an error of ca$\pm 3\times 10^{-3}$) may be determined by ICP (metal) analysis.

The catalysts may be, for example, AlPO-5, 18, 31, 36 or 37 type, preferably of the $M^1M^2$AlPO-5, $M^1M^2$AlPO-18 or $M^1M^2$AlPO-36 type, but are preferably of the $M^1M^2$AlPO-5 type. Specific preferred examples of these catalysts for use in the ammoximation of cyclohexanone are $Co^{III}Mn^{III}$AlPO-5, $Co^{III}Fe^{III}$AlPO-5, and $Mn^{III}Fe^{III}$AlPO-5.

In the process of the present invention a ketone or aldehyde is reacted with ammonia and oxygen. The ketone or aldehyde may be any ketone or aldehyde, for example a $C_3$-$C_{20}$ ketone or $C_2$-$C_{20}$ aldehyde, and may be linear, branched or cyclic. Preferred ketones are cyclic ketones, for example $C_5$-$C_{12}$ cyclic ketones, with $C_6$ and $C_{12}$ ketones being the most preferred. Preferred aldehydes contain a cyclic or aromatic ring, especially a $C_6$ ring. A preferred aldehyde is benzaldehyde. The ketone or aldehyde may be unsubstituted or substituted, for example by a $C_1$-$C_4$ alkyl or alkenyl group, —OH or halogen. The ammonia may be in the form of a gas or dissolved in a solvent such as water. Preferably it is in the form of aqueous ammonium hydroxide. Other than the water present from the aqueous ammonium hydroxide, no additional solvent is normally needed but it may be used if desired. The oxygen is provided in the form of a gas, for example as $O_2$ or air.

The reaction product is generally an oxime corresponding to the ketone or aldehyde starting material. Thus, for example, the present invention can be used for the ammoximation of cyclohexanone to cyclohexanone-oxime, which is a precursor to ε-caprolactam, ε-caprolactam itself being an important precursor to nylon-6, for which there is a large and growing market, and so this reaction is particularly preferred. It can also be used for the ammoximation of benzaldehyde to benzaldehyde-oxime. In this reaction, cyclohexanone or benzaldehyde is reacted with ammonia (generally and preferably in the form of aqueous ammonium hydroxide) and oxygen (which may be provided in the form of pure oxygen or air) in the presence of the catalyst.

The reaction will take place over a wide range of temperatures and pressures, and the exact temperature and pressure chosen is not critical to the present invention. However, we generally prefer to carry out the reaction with heating, e.g. a temperature in the range from 50 to 95° C., more preferably from 70 to 90° C. A pressure of, for example, from 1 to 500 atmospheres is preferably used, more preferably 1 to 100 atmospheres and most preferably 1 to 10 atmospheres. The oxime produced may be converted into other compounds, for example a lactam. A suitable method is described in PNAS 102 (39) 13732-13736 using the Beckmann rearrangement using oleum followed by an acid such as sulphuric acid.

The process of the present invention provides the oxime product in an unexpectedly high conversion rate and at good selectivity. The data in Table 1 of J. Am. Chem. Soc. 2001, 123, 8153-4 shows a conversion rate at 6 hours of up to 20%. The process of the present invention achieves a conversion rate of at least 50%, preferably at least 70%, as described in the following Examples.

EXAMPLES

General Experimental Setup and Analytical Protocols

The catalytic reactions were carried out in a stainless-steel catalytic reactor (100 ml, Parr) lined with Poly Ether Ether Ketone (PEEK). The substrate (cyclohexanone), ammonia (28% ammonium hydroxide in double-distilled deionised water) a suitable internal standard (adamantane) and the catalyst (e.g. $Co^{III}Mn^{III}$AlPO-5, which was inserted into the sphere of reaction using a specially-designed catalyst delivery system) were then introduced into the reactor, which was subsequently sealed. The reactor and the inlet and outlet ports were purged thrice with dry nitrogen prior to reaction. The reactor was then pressurised with the oxidant (dry air or pure oxygen under dynamic pressure) and the contents were heated to the desired temperature under constant stirring.

At the end of the reaction, the heating was turned off and the contents of the reactor were cooled (quenched). The reactor was depressurised and a mass-balance calculation was performed at this stage to check for handling and mass losses. Where kinetic and rate effects were studied, a mini-robot liquid sampling valve was employed to remove small aliquots (0.1 μl) of the sample (aqueous and organic phases) during the course of the reaction. The products were analyzed either online (using a robotically-controlled unit with an online computer-controlled system which is linked to a GC and/or LCMS) or offline (using a suitable internal standard) by gas chromatography (GC, Varian, Model 3400 CX) employing a HP-1 capillary column (25 m×0.32 mm) and flame ionisation detector using a variable ramp temperature program (from 50° C. to 300° C.). In the offline analysis method, the products were separated and the organic layer was dried using magnesium sulphate prior to GC analysis. The identities of the products were first confirmed using authenticated standards and their individual response factors were determined using a suitable internal standard (adamantane) by the calibration method. The overall yields were normalized with respect to the (GC) response factors obtained as above.

The conversions and selectivities were determined as defined by the following equations and the yields were normalised with respect to the response factors obtained as above:

Conv. %=[(moles of initial substrate−moles of residual substrate)/(moles of initial substrate)]×100

Sel. %=[(moles of individual product)/(moles of total products)]×100

For the internal standard GC method, the response factor (RF) and mol % of individual products were calculated using the following equations:

RF=(mol Product/mol Standard)×(Area Standard/Area Product)

Mol % Product=RF×Mol Standard×(Area Product/Area Standard)×100/Mol Sample

The identity of the products was further confirmed using LCMS (Shimadzu LCMS-QP8000), which was again employed either online or offline. Hot filtration experiments and ICP measurements of the aqueous and organic mixtures were independently carried out to check for the occurrence of leaching.

Example 1

Ammoximation of Cyclohexanone Using $Co^{III}Mn^{II}$-$_iAlPO$-5

This experiment was performed using the protocol described above using 25 g of cyclohexanone, 14.6 g of ammonia, 0.5 g of adamantane (the internal standard), 0.75 of $Co^{III}Mn^{III}AlPO$-5 (0.10), 30 bar of dry air at 353 K for 6 hours.

The conversion of cyclohexanone to oxidised products was calculated to be 77% and the selectivity for cyclohexanone oxime was 88%.

Example 2

Ammoximation of Cyclohexanone Using $Co^{III}Mn^{II}$-$_iAlPO$-5

This experiment was performed using the protocol described above using 25 g of cyclohexanone, 14.6 g of ammonia, 0.5 g of adamantane (the internal standard), 0.75 of $Co^{III}Mn^{III}AlPO$-5 (0.10), 15 bar of pure oxygen at 353 K for 6 hours.

The conversion of cyclohexanone to oxidised products was calculated to be 71% and the selectivity for cyclohexanone oxime was 84%.

Example 3

Ammoximation of Cyclohexanone Using $Co^{III}Fe^{II}$-$_iAlPO$-5

This experiment was performed using the protocol described above using 25 g of cyclohexanone, 14.6 g of ammonia, 0.5 g of adamantane (the internal standard), 0.5 of $Co^{III}Fe^{III}AlPO$-5 (0.10), 30 bar of dry air at 353 K for 6 hours.

The conversion of cyclohexanone to oxidised products was calculated to be 56% and the selectivity for cyclohexanone oxime was 89%.

Example 4

Ammoximation of Cyclohexanone Using $Mn^{III}Fe^{II}$-$_iAlPO$-5

This experiment was performed using the protocol described above using 25 g of cyclohexanone, 14.6 g of ammonia, 0.5 g of adamantane (the internal standard), 0.5 of $Mn^{III}Fe^{III}AlPO$-5 (0.10), 30 bar of dry air at 353 K for 6 hours.

The conversion of cyclohexanone to oxidised products was calculated to be 78% and the selectivity for cyclohexanone oxime was 92%.

Example 5

Ammoximation of Cyclohexanone Using $Co^{III}Mn^{II}$-$_iAlPO$-5

This experiment was performed using the protocol described above using 15 g of cyclohexanone, 14.6 g of ammonia, 0.5 g of adamantane (the internal standard), 0.75 of $Co^{III}Mn^{III}AlPO$-5 (0.10), 30 bar of dry air at 373 K for 6 hours.

The conversion of cyclohexanone to oxidised products was calculated to be 91% and the selectivity for cyclohexanone oxime was 86%.

Example 6

Ammoximation of Cyclohexanone Using $Co^{III}Mn^{II}$-$_iAlPO$-5

This experiment was performed using the protocol described above using 15 g of cyclohexanone, 29.2 g of ammonia, 0.5 g of adamantane (the internal standard), 1.0 of $Co^{III}Mn^{III}AlPO$-5 (0.10), 30 bar of dry air at 353 K for 6 hours.

The conversion of cyclohexanone to oxidised products was calculated to be 95% and the selectivity for cyclohexanone oxime was 84%.

Example 7

Ammoximation of Cyclohexanone Using $Co^{III}Mn^{II}$-$_iAlPO$-5

This experiment was performed using the protocol described above using 14.6 g of ammonia, 0.5 g of adamantane (the internal standard), 0.75 of $Co^{III}Mn^{III}AlPO$-5 (0.10), 30 bar of dry air at 353 K for 6 hours.

At the end of the reaction, the heating was turned off and the contents of the reactor were cooled (quenched). The reactor was depressurised and a mass-balance calculation was performed at this stage to check for handling and mass losses. 15 g of cyclohexanone, dissolved in 20 g of toluene was then added to the above reaction mixture and the contents were stirred for a further 60 minutes at 298 K under nitrogen (5 bar) in the same reactor. The reactor was then cooled to room temperature before depressurising. A mass-balance analysis was carried out at the stage to check for handling and other losses. The organic components were then separated and dried using magnesium sulphate. The analysis was then performed as described earlier in the protocol above.

The conversion of cyclohexanone to oxidised products was calculated to be 86% and the selectivity for cyclohexanone oxime was 100%.

Example 8

Ammoximation of Cyclohexanone Using $Co^{III}Mn^{II}$-$_iAlPO$-5

This experiment was performed using the protocol described above using 29.2 g of ammonia, 0.5 g of adamantane (the internal standard), 0.75 of $Co^{III}Mn^{III}AlPO$-5 (0.10), 30 bar of dry air at 353 K for 6 hours.

At the end of the reaction, the heating was turned off and the contents of the reactor were cooled (quenched). The reactor was depressurised and a mass-balance calculation was performed at this stage to check for handling and mass losses. 15 g of cyclohexanone, dissolved in 20 g of toluene was then added to the above reaction mixture and the contents were stirred for a further 60 minutes at 298 K under nitrogen (5 bar) in the same reactor. The reactor was then cooled to room temperature before depressurising. A mass-balance analysis was carried out at the stage to check for handling and other losses. The organic components were then separated and dried using magnesium sulphate. The analysis was then performed as described earlier in the protocol above.

The conversion of cyclohexanone to oxidised products was calculated to be 88% and the selectivity for cyclohexanone oxime was 100%.

Example 9

Ammoximation of Cyclohexanone Using $Co^{III}Fe^{II}$-$t$AlPO-5

This experiment was performed using the protocol described above using 14.6 g of ammonia, 0.5 g of adamantane (the internal standard), 0.75 of $Co^{III}Fe^{III}$AlPO-5 (0.10), 30 bar of dry air at 353 K for 6 hours.

At the end of the reaction, the heating was turned off and the contents of the reactor were cooled (quenched). The reactor was depressurised and a mass-balance calculation was performed at this stage to check for handling and mass losses. 15 g of cyclohexanone, dissolved in 20 g of toluene was then added to the above reaction mixture and the contents were stirred for a further 60 minutes at 298 K under nitrogen (5 bar) in the same reactor. The reactor was then cooled to room temperature before depressurising. A mass-balance analysis was carried out at the stage to check for handling and other losses. The organic components were then separated and dried using magnesium sulphate. The analysis was then performed as described earlier in the protocol above.

The conversion of cyclohexanone to oxidised products was calculated to be 81% and the selectivity for cyclohexanone oxime was 100%.

Example 10

Ammoximation of Cyclohexanone Using $Mn^{III}Fe^{II}$-$t$AlPO-5

This experiment was performed using the protocol described above using 14.6 g of ammonia, 0.5 g of adamantane (the internal standard), 0.75 of $Mn^{III}Fe^{III}$AlPO-5 (0.10), 30 bar of dry air at 353 K for 6 hours.

At the end of the reaction, the heating was turned off and the contents of the reactor were cooled (quenched). The reactor was depressurised and a mass-balance calculation was performed at this stage to check for handling and mass losses. 15 g of cyclohexanone, dissolved in 20 g of toluene was then added to the above reaction mixture and the contents were stirred for a further 60 minutes at 298 K under nitrogen (5 bar) in the same reactor. The reactor was then cooled to room temperature before depressurising. A mass-balance analysis was carried out at the stage to check for handling and other losses. The organic components were then separated and dried using magnesium sulphate. The analysis was then performed as described earlier in the protocol above.

The conversion of cyclohexanone to oxidised products was calculated to be 94% and the selectivity for cyclohexanone oxime was 100%.

Example 11

Ammoximation of Cyclohexanone Using $Co^{III}Mn^{II}$-$t$AlPO-5

This experiment was performed using the protocol described above using 29.2 g of ammonia, 0.5 g of adamantane (the internal standard), 0.75 of $Co^{III}Mn^{III}$AlPO-5 (0.10), 30 bar of dry air at 373 K for 8 hours.

At the end of the reaction, the heating was turned off and the contents of the reactor were cooled (quenched). The reactor was depressurised and a mass-balance calculation was performed at this stage to check for handling and mass losses. 15 g of cyclohexanone, dissolved in 20 g of toluene was then added to the above reaction mixture and the contents were stirred for a further 60 minutes at 298 K under nitrogen (5 bar) in the same reactor. The reactor was then cooled to room temperature before depressurising. A mass-balance analysis was carried out at the stage to check for handling and other losses. The organic components were then separated and dried using magnesium sulphate. The analysis was then performed as described earlier in the protocol above.

The conversion of cyclohexanone to oxidised products was calculated to be 97% and the selectivity for cyclohexanone oxime was 94%.

The invention claimed is:

1. A redox ammoximation process comprising reacting a ketone with ammonia and oxygen in the presence of a catalyst to form a cyclohexanone-oxime; wherein
the catalyst is an aluminophosphate based redox catalyst having
the formula (I):

$$M^1M^2AlPO\text{-}5 \qquad (I)$$

wherein $M^1$ and $M^2$ each represents a different atom selected from Co(III), Mn(III) and Fe(III).

2. A process according to claim 1 wherein the catalyst is $Co^{III}Mn^{III}$AlPO-5, $Co^{III}Fe^{III}$AlPO-5 or $Mn^{III}Fe^{III}$AlPO-5.

3. A process according to claim 1 wherein the ammonia is in the form of aqueous ammonium hydroxide.

4. A process according to claim 1 further comprising carrying out the process at a temperature in the range from 50 to 95° C.

5. A process according to claim 4 further comprising carrying out the process at a temperature in the range from 70 to 90° C.

* * * * *

UNITED STATES PATENT AND TRADEMARK OFFICE
CERTIFICATE OF CORRECTION

PATENT NO. : 8,450,526 B2  
APPLICATION NO. : 12/666343  
DATED : May 28, 2013  
INVENTOR(S) : Raja et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 136 days.

Signed and Sealed this
Eighth Day of September, 2015

Michelle K. Lee
*Director of the United States Patent and Trademark Office*